United States Patent [19] [11] Patent Number: 6,153,755
Ennis et al. [45] Date of Patent: *Nov. 28, 2000

[54] PROCESS FOR PREPARING PHARMACEUTICALLY ACTIVE COMPOUNDS AND INTERMEDIATES THEREOF

[75] Inventors: David S. Ennis, Buntingford, United Kingdom; David Charles Lathbury, Malvern, Pa.

[73] Assignee: SmithKline Beecham plc, Brentford, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/966,993

[22] Filed: Nov. 10, 1997

[30] Foreign Application Priority Data

Nov. 9, 1996 [GB] United Kingdom .................. 9623359

[51] Int. Cl.$^7$ ...................... C07D 211/22; C07D 211/58; C07D 498/04
[52] U.S. Cl. ........................... 546/240; 546/115; 546/223
[58] Field of Search ................... 546/240, 223, 546/115

[56] References Cited

U.S. PATENT DOCUMENTS

| | | | |
|---|---|---|---|
| 4,007,196 | 2/1977 | Christensen et al. | 546/197 |
| 4,585,777 | 4/1986 | Lassen et al. | 514/317 |
| 4,593,036 | 6/1986 | Lassen et al. | 546/236 |
| 4,861,893 | 8/1989 | Borrett | 546/185 |
| 4,902,801 | 2/1990 | Faruk et al. | 546/220 |
| 5,039,803 | 8/1991 | Smith et al. | 546/185 |
| 5,258,517 | 11/1993 | Zepp et al. | 546/240 |
| 5,328,917 | 7/1994 | Jakonson et al. | 514/331 |
| 5,665,736 | 9/1997 | Forguet et al. | 514/321 |
| 5,681,962 | 10/1997 | Callander | 546/219 |

FOREIGN PATENT DOCUMENTS

| | | |
|---|---|---|
| 0 190 496 | 8/1986 | European Pat. Off. . |
| 0 300 617 | 1/1989 | European Pat. Off. . |
| 0 374 674 | 6/1990 | European Pat. Off. . |
| 0 812 827 | 12/1997 | European Pat. Off. . |
| WO 96/36636 | 11/1996 | WIPO . |

OTHER PUBLICATIONS

Micovic et al., J. Chem. Soc., Perk Trans. 1, No. 16, pp. 2041–2050 (1996).
Carey, Organic Chemistry, McGraw–Hill Book Co., p. 566 (1987).

Primary Examiner—Bernard Dentz
Attorney, Agent, or Firm—Wayne J. Dustman; William T. King; Charles M. Kinzig

[57] ABSTRACT

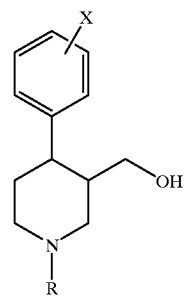

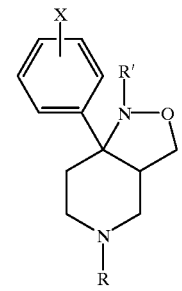

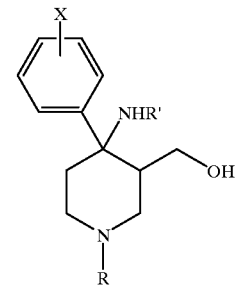

A process is disclosed for the preparation of (1) by reduction of (2) directly using catalytic transfer hydrogenation to suppress formation of (4) or by conventional reduction via (4). Compound (1) is a key intermediate for inter alia paroxetine.

10 Claims, No Drawings

PROCESS FOR PREPARING PHARMACEUTICALLY ACTIVE COMPOUNDS AND INTERMEDIATES THEREOF

The present invention relates to a new process for preparing pharmaceutically active compounds and intermediates therefor.

Pharmaceutical products with antidepressant and anti-Parkinson properties are described in U.S. Pat. No. 4,007,196. An especially important compound among those disclosed is paroxetine.

This invention aims to overcome disadvantages in the existing processes for preparation of such compounds and so to provide alternative processes for their manufacture.

This invention has been developed on the basis that compounds of structure (1) below are valuable chemical intermediates useful for the manufacture of important medicinal products, for example paroxetine hydrochloride.

By reference to Example 4 of U.S. Pat. No. 4,007,196, paroxetine may be prepared from a compound of structure (1) below in which R is methyl and X is 4-fluoro, that is 4-(4'-fluorophenyl)-3-hydroxymethyl-1-methylpiperidine, by reaction with 3,4-methylenedioxyphenol followed by demethylation. In the same Example, 4-(4'-fluorophenyl)-3-hydroxymethyl-1-methyl piperidine is prepared by reduction of 4-(4'-fluorophenyl)-3-hydroxymethyl-1-methyl-1,2,3,6-tetrahydropyridine (II), which is in turn prepared from 4-(4'-fluorophenyl)-1-methyl-1,2,3,6-tetrahydropyridine (III), by reaction with formaldehyde.

In EP-A-0152273, compound (II) is prepared by a process in which an α-methyl styrene is reacted with formaldehyde and an amine hydrochloride, via compound (III) as an non-isolated intermediate. Known methods for converting compound (III) into compound (II) are inefficient, and the product (II) has been shown to contain approximately 30% residual compound (III). This is carried forward and causes problems with subsequent stages and with residues in the finally intended product. Furthermore, the use of both hydrochloric acid and formaldehyde can give rise to bis-chloromethylether.

Paroxetine is the (−) trans isomer of 4-(4'-fluorophenyl)-3-(3',4'-methylenedioxyphenoxymethyl)-piperidine. The above described processes produce compounds of structure (1) as a mixture of enantiomers. Therefore conversion of compounds of structure (1) to useful pharmaceuticals will normally require a resolution stage, as described in EP-A-0223334.

This invention provides a process for the preparation of a 4-aryl-3-hydroxymethylpiperidine of structure (1)

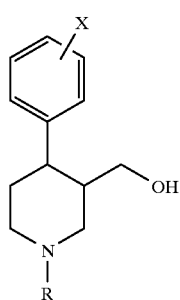

(1)

in which R and X are as indicated below, which comprises reducing an isoxazolidine of structure (2).

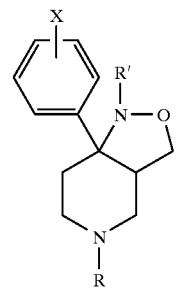

(2)

in which R' is as indicated below.

In the above structure, R and R' groups may be the same or different hydrogen, alkyl, arylalkyl, allyl, carbonyloxyalkyl, carbonyloxyaryl, or carbonyloxyalkylaryl groups where appropriate to the reactions described below. R is most suitably lower alkyl or allyl. R' is most suitably hydrogen for reduction of compounds of structure (2) to compounds of structure (1), but may be a chiral auxiliary when a compound of structure (2) is prepared by an enantioselective synthesis as discussed below. X is one or more of hydrogen, halogen (especially fluoro), hydroxy, alkoxy, nitro, nitrile, amino (optionally protected or substituted), trifluoromethyl, acyl, formyl, carboxyl or carboxyalkyl.

Among the substituents suitable for R and X, alkyl groups (including alkyl groups as part of arylalkyl and the indicated acyl groups) are typically lower or $C_{1-6}$ alkyl groups, such as methyl, ethyl, n-propyl, iso-propyl, n-butyl or iso-butyl. Aryl groups (including aryl groups as part of arylalkyl and the indicated acyl groups) are typically phenyl and are optionally substituted, for example by nitro, halogen, phenyl or a $C_{1-6}$ alkyl or alkoxy group. Arylalkyl groups are typically benzyl or substituted benzyl.

Conversion of compounds of structure (2) into 3-hydroxymethylpiperidines of structure (1) requires forcing reducing conditions to avoid contamination with intermediate 4-amino-4-aryl-3-hydroxymethylpiperidines of structure (4).

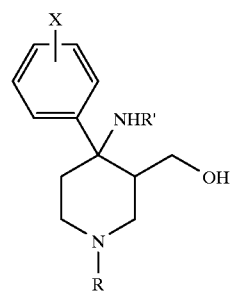

(4)

Suitable reducing conditions include catalytic transfer hydrogenation with, for example, palladium on charcoal and ammonium formate. Under these conditions the product is exclusively the cis-isomer, but this is not a disadvantage for use as an intermediate in the production of pharmaceutically active ethers such as paroxetine since coupling by displacement of a sulphonyl ester is believed to proceed via a quaternary ammonium cyclic intermediate and results in almost exclusively the trans ether. However, reduction leading to trans compounds of structure (1) can be achieved with other catalysts.

The compounds of structure (2) and the 4-amino-4-aryl-3-hydroxymethylpiperidines of structure (4) that may be obtained as intermediates during reduction of compounds of structure (2) are believed to be novel and form part of this invention. This invention also includes the transformation of compounds of structure (4), obtained by reduction of compounds of structure (2) or by alternative means, to compounds of structure (1).

One advantageous aspect of the process of this invention is that a single enantiomer of the intermediate (2) may be prepared from a chiral precursor, thereby transferring the resolution, normally required after coupling with the aryl moiety, to a very early stage in the overall process.

Compounds of structure (2) in which R' is hydrogen may be prepared by the reaction of an appropriately substituted organometallic phenyl derivative with an isoxazoline of structure (3),

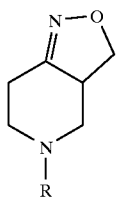

(3)

in which R is as defined above. One suitable reagent for this transformation is the lithium derivative obtained from 4-fluorobromobenzene. R' groups other than hydrogen may introduced into the R'=H compound by conventional substitutions.

Other methods for the preparation of compounds of structure (2) include cyclisation of a nitrone obtained from an aryl 3-allylaminoethyl ketone oxime by Grigg methodology.

By using a R' substituent which is a chiral auxiliary in this reaction, resolution may be avoided in subsequent processing.

Compounds of structure (3) may be resolved by conventional methods to provide a chiral precursor for the subsequent reactions described above. In those cases where R is hydrogen, alkyl, allyl, or arylalkyl, a conventional chiral acid resolving agent may be used, for example dibenzoyl-D-tartaric acid when R is allyl.

The compound of structure (3) may be prepared by intramolecular cycloaddition of a nitrile oxide obtained, for example, by oxidation of a 3-(allylamino)-propionaldehyde oxime, which may in turn be prepared by base catalysed addition of an alkyl or arylalkyl substituted allyl amine to acrolein.

In a further aspect of the invention, a compound of structure (1) obtained by processes of this invention may be converted to an active compound disclosed in U.S. Pat. No. 4,007,196 using conventional procedures disclosed therein.

In particular the compound of structure (1) in which X is 4-fluoro may be used to prepare paroxetine. The paroxetine is preferably obtained as the hydrochloride salt and most preferably as the hemihydrate of that salt, as described in EP-A-0223403.

The present invention includes within its scope the compound paroxetine, particularly paroxetine hydrochloride, especially as the hemihydrate, when obtained via any aspect of this invention, and any novel intermediates resulting from the described procedures.

The various aspects of this invention are illustrated by the following Examples.

EXAMPLE 1

A solution of acrolein (55 ml) in tetrahydrofuran (50 ml) was added slowly, over 25 minutes, to a solution of diallylamine (90 ml) and DBU (0.88 ml) in tetrahydrofuran (300 ml) at a temperature of approximately −10° C. The mixture was stirred at −15° C. for an hour, at which point a solution of sodium hydroxide (30 g) and hydroxylamine hydrochloride (50 g) in water (200 ml) was slowly added over 30 minutes keeping the temperature below 5° C. n-Hexane (300 ml) was added and the reaction allowed to warm up to ambient temperature with stirring. The mixture was extracted with more n-hexane (300 ml) and the combined organic phases washed twice with water (2×50 ml), dried over anhydrous magnesium sulphate, and evaporated under reduced pressure to a yellow oil (121.2 g).

A solution of the yellow oil (1.0 g) in dichloromethane (10 ml) was treated at 20° C. with sodium hypochlorite solution (0.45 g, 8% chlorine equivalent, hence 2.6 ml solution), to give an exothermic reaction. The reaction was monitored by t.l.c. and further portions of sodium hypochlorite were added until the reaction was complete (17.5 ml required in total). The dichloromethane phase was separated, washed with water (5 ml), dried with anhydrous magnesium sulphate, and evaporated. The residue was washed through a silica plug with ethyl acetate, and the solvent evaporated to produce a compound of structure (3), in which R is allyl, as a pale yellow oil (0.47 g).

EXAMPLE 2

4-fluorobromobenzene (1.32 ml) was dissolved in tetrahydrofuran (18 ml) and slowly treated with tertiary butyl lithium solution (10.85 ml, 1 equivalent) at −78° C. over 10 minutes. The isoxazoline (compound (3) where R is allyl, 1.0 g) in tetrahydrofuran (2 ml) was added over 5 minutes at −78° C. and stirred at this temperature for 2 hours, then allowed to warm to ambient temperature and stirred for a further hour. The mixture was then acidified to pH 2 with hydrochloric acid, diluted with water (20 ml) and extracted with ethyl acetate (20 ml). The aqueous phase was separated, adjusted to pH 9 with aqueous sodium hydroxide solution (2 molar), and extracted twice with ethyl acetate (2×10 ml). The ethyl acetate extracts were combined, dried over anhydrous magnesium sulphate, and evaporated at reduced pressure to produce the isoxazolidine of structure (2) in which R is allyl.

Yield 1.28 g (82%). Mass spectrum $(M+H)^+$, $M/Z=263$.

EXAMPLE 3

The isoxazolidine product of Example 2 (1.0 g) was dissolved in methanol (80 ml) together with ammonium formate (4.82 g) and heated at reflux for 48 hours with palladium on carbon catalyst (0.5 g). The reaction mixture was filtered through celite and the solvent removed by evaporation at reduced pressure to produce 1-allyl-4-(4'-fluorophenyl)-3-hydroxymethylpiperidine as a yellow oil, 0.59 g (62%).

We claim:

1. A process for preparation of a 4-aryl-3-hydroxymethyl-piperidine of structure (1)

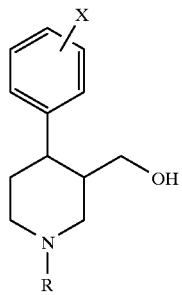
(1)

in which R is hydrogen, alkyl, arylalkyl, allyl, carbonyloxyalkyl, carbonyloxyaryl, or carbonyloxyalkylaryl, and X is one or more of hydrogen, halogen, hydroxy, alkoxy, nitro, nitrile, amino (optionally protected or substituted), trifluoromethyl, acyl, formyl, carboxyl or carboxyalkyl, which comprises reducing an isoxazolidine of structure (2)

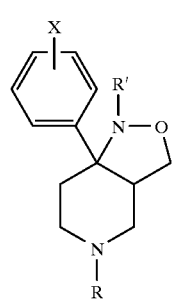
(2)

or a compound of structure (4)

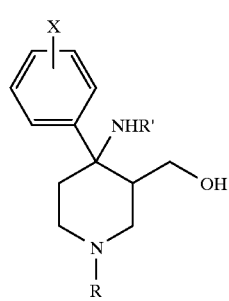
(4)

in which R and X are as defined above, and R' is independently selected from the same groups as R or is a chiral auxiliary.

2. A process according to claim 1, in which the reduction of a compound of structure (2) or structure (4) is carried out by catalytic transfer hydrogenation.

3. A process according to claim 2, in which the catalytic transfer hydrogenation is carried out with palladium on charcoal and ammonium formate.

4. A process according to claim 1, in which the compound of structure (4) is prepared by reduction of a compound of structure (2).

5. A process according to claim 1, in which the compound of structure (2) is prepared by the reaction of an X-substituted phenyl organometallic derivative with an isoxazoline of structure (3),

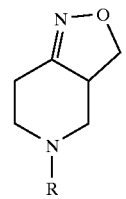
(3)

in which X and R are as defined above.

6. A process according to claim 5, in which a R' substituent which is other than hydrogen is introduced into the compound of structure (2) before further reaction.

7. A compound of structure (2) or (4)

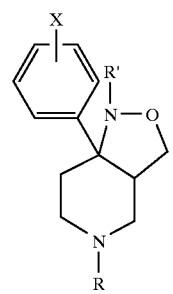
(2)

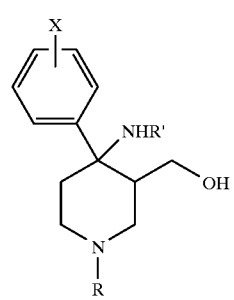
(4)

in which R is hydrogen, alkyl, arylalkyl, allyl, carbonyloxyalkyl, carbonyloxyaryl, or carbonyloxyalkylaryl, R' is independently selected from the same groups as R or is a chiral auxiliary, and X is one or more of hydrogen, halogen, hydroxy, alkoxy, nitro, nitrile, amino (optionally protected or substituted), trifluoromethyl, acyl, formyl, carboxyl or carboxyalkyl.

8. A process for preparing paroxetine comprising obtaining a compound of structure (1) in which X is 4-fluoro by a process as claimed in claim 1, reacting the compound of structure (1) with 3,4-methylenedioxyphenol, and if necessary replacing the substituent R with a hydrogen atom.

9. A process according to claim 8, in which paroxetine is obtained as, or converted to, a hydrochloride salt.

10. A process according to claim 9, in which the paroxetine hydrochloride salt is obtained as the hemihydrate.

* * * * *